United States Patent
Féré et al.

[11] Patent Number: 6,135,172
[45] Date of Patent: Oct. 24, 2000

[54] DEVICE FOR SAMPLING AND/OR INJECTING INSIDE A PLUGGED SAMPLE TUBE

[75] Inventors: Patrick Féré, Paris; Patrick Perin, Saint Cyr l'Ecole Henry; Alain Rousseau, Paris, all of France

[73] Assignee: Junior Instruments, France

[21] Appl. No.: 09/284,606

[22] PCT Filed: Jul. 30, 1998

[86] PCT No.: PCT/FR98/01734

§ 371 Date: Apr. 19, 1999

§ 102(e) Date: Apr. 19, 1999

[87] PCT Pub. No.: WO99/09389

PCT Pub. Date: Feb. 25, 1999

[30] Foreign Application Priority Data

Aug. 20, 1997 [FR] France ................................. 97 10566

[51] Int. Cl.[7] .......................... G01N 1/00; G01N 35/10; B01L 3/00; A61M 5/162; B67C 3/00

[52] U.S. Cl. .............................. 141/329; 141/59; 141/94; 141/130

[58] Field of Search .................. 141/25–27, 59, 141/94, 130, 329, 330

[56] References Cited

U.S. PATENT DOCUMENTS 5,102,623   4/1992   Yamamoto et al. .................... 141/130

Primary Examiner—J. Casimer Jacyna
Attorney, Agent, or Firm—William A. Drucker

[57] ABSTRACT

The invention concerns a hollow needle axially mobile so as to pierce a container stopper. Said needle comprises a pointed end with a cutting edge tangent to the needle cylindrical body generatrix, an oblique shape linking the edge to said cylindrical body and a side outlet orifice of the channel centred on said generatrix and a site spaced from the edge, said orifice being centred perpendicular to the needle longitudinal axis. This invention is applicable to automatic and semiautomatic analytical equipment.

9 Claims, 2 Drawing Sheets

DEVICE FOR SAMPLING AND/OR INJECTING INSIDE A PLUGGED SAMPLE TUBE

BACKGROUND OF THE INVENTION

1. Field of the Invention

This invention relates to a device intended for the taking of samples and/or injection inside sealed receptacles such as e.g. test tubes sealed with plastic stoppers.

2. Description of the Prior Art

Generally, it is known that for security and precision purposes, numerous analysis processes and especially in biological processes, we use sample tubes plugged with rubber (or more generally plastomer) bungs, in order to be able to perform all manipulations pertaining to these processes without having to remove the stopper and therefore without direct access to the sample. In the case of hematological analyses, increasingly frequent use is made of sealed test tubes in which a relative vacuum is created enabling the use of a syringe to be avoided when taking a blood sample, the blood being directly drawn into the tube under the effect of the depression.

The taking of samples and/or injections performed into these tubes then entails the use of devices each comprising a hollow needle connected to a suction and/or delivery pipe.

When it equips an automated analysis system, the sampling device is borne by a pipeting head equipped with means ensuring vertical displacement of the needle, and possibly mobile above a pipeting area in which a plurality of sample tubes is arranged. It is obvious that in this case the needle must be capable of performing a multiplicity of piercings and samplings without the precision of the device being affected.

In practice it transpires that the perfecting of such a device and the design of such sampling needles give rise to numerous problems.

Thus, the use of conventional hollow needles with substantially cone-shaped tapered tips is not really suitable for automated or semi-automated analysis systems for the following reasons:

- during piercing of the stopper, these needles perform like hollow punches, cutting out in the stopper a circular portion of cross-section substantially equal to the cross-section of the needle channel: this circular portion engages in the channel and causes at least partial obturation thereof. Accordingly, during the suction phase, this portion generates a more or less considerable loss of head that constitutes a first source of error on the quantities sampled off (which must be constant for each sampling);
- during the piercing action, the stopper is subjected to a deformation causing a pressure variation (excess pressure) inside the receptacle, said variation constituting a second source of error concerning the quantities sampled off. Likewise, during extraction of the needle, the deformation of the stopper in the opposite direction generates a depression which brings about a suction effect tending to aspirate the liquid sampled off. The imprecision resulting from these two phenomena is amplified by the fact that the level of the sample inside the tube is variable from one tube to another and that, therefore, the values of the excess pressure and depression cannot be determined;
- The hollow punch effect leads to the formation of bores that close up poorly after extraction of the needle, as a result of which the tightness of the seal can no longer be guaranteed.

In order to remedy the problems pertaining to the imprecision of the quantities sampled off, it has been proposed that use be made of sampling devices using electrovalve sets enabling the performance of complex sampling sequences taking into account the above-mentioned parameters. However, this solution has proved costly, not very reliable and yet does not solve all the above-mentioned drawbacks.

OBJECT OF THE INVENTION

The main object of this invention is to provide a simple, relatively inexpensive and yet efficient solution to these problems.

SUMMARY OF THE INVENTION

Accordingly, there is provided a sampling device using a hollow needle that is axially mobile so as to be capable of perforating a stopper sealing the receptacle in which the sample to be sampled off is contained.

According to the invention, this device is characterized in that the pointed tip of the needle comprises at least one cutting edge at a tangent to a generating line of the cylindrical body of the needle, an oblique shape connecting the edge to said cylindrical body and a lateral outlet hole of the channel centered on said generating line at a location distant from the edge, this hole being angled perpendicularly to the longitudinal axis of the needle.

Advantageously, the aforesaid edge and hole extend in a same plane at a tangent to said generating line.

According to a preferred embodiment of the invention, the aforesaid oblique shape constitutes a cranking of the end of the cylindrical body whereas said tangential plane is a machined plane perpendicular to the plane of symmetry of the cranking.

According to another feature of the invention, the cylindrical body of the needle comprises, in its outer cylindrical surface, at least one axial groove ending at a predetermined distance from the tip of the needle. Preferably, this groove, which is intended to aerate the interior volume of the sample during sampling off, is of square or rectangular cross-section.

BRIEF DESCRIPTION OF THE DRAWINGS

An embodiment of the invention will now be described, by way of a non-limiting example, in reference to the corresponding accompanying drawings in which.

DESCRIPTION OF THE PREFERRED EMBODIMENTS

Figure 1:
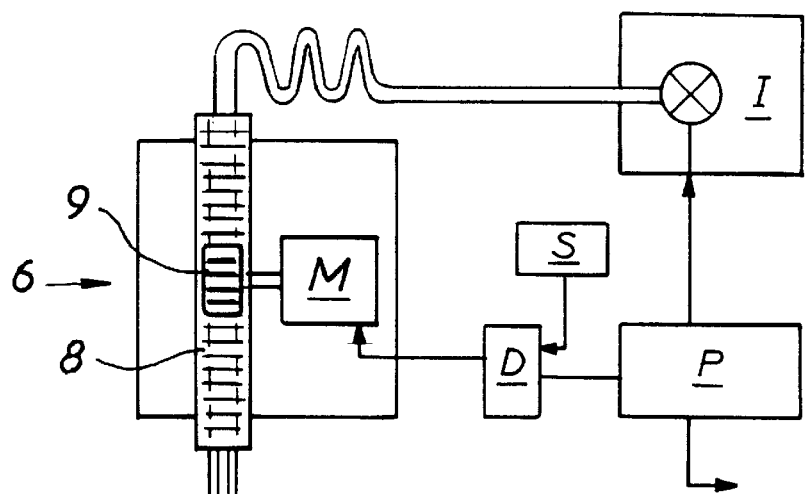
FIG. 1 is a schematic representation of a conventional sampling device.
Figure 1:
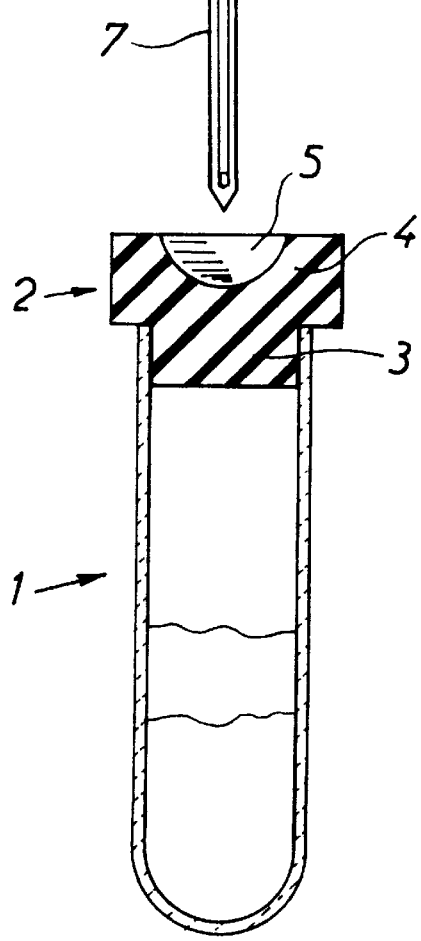

In the example represented in FIG. 1, the receptacle containing the sample to be analyzed consists of a conventional type glass tube 1 sealed by a rubber stopper or bung 2 comprising a cylindrical body 3 of diameter slightly greater than the interior diameter of the tube 1, and a cap 4 which is also cylindrical and of diameter greater than the outer diameter of the tube 1. The upper side of the cap 4 comprises a spherical recess 5 intended to reduce the thickness of the central region where the piercing takes place. Of course, the body 3 fits tightly into the tube 1 while the cap 4 forms, with the body 3, a shoulder against which the upper rim of tube 1 abuts.

In the axis of the tube 1 is represented a pipeting head 6 which is perpendicularly mobile in relation to said axis and which comprises a mechanism actuating a needle 7 angled parallel to said axis.

This mechanism comprises a rack 8 integral with the needle and meshing with a pinion 9 driven by a direct-current electric motor M powered by an electric current source S whose intensity and/or voltage characteristics are measured by a detector D prior to being transmitted to a processor P which controls the device. As for the needle 7, it is connected to a sampling/injecting circuit I also driven by the microprocessor P.

The operation of this device is as follows: during a sampling and/or injecting phase, the pipeting head 6 positions itself above the tube 1, the needle 7 being situated in the longitudinal axis of the tube 1.

The processor P then commands the motor to turn so as to bring about a displacement of the rack 8 and therefore of the needle 7 to which it is secured.

Figure 2:
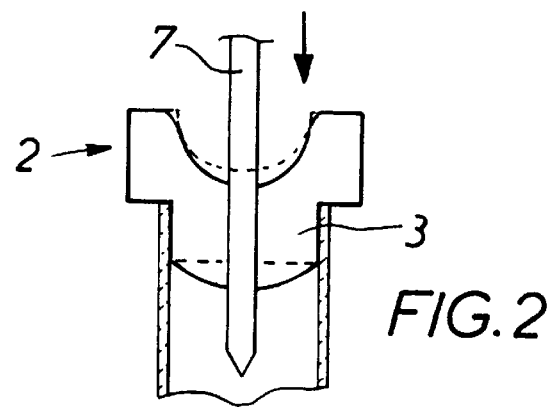
FIGS. 2 and 3 are partial views illustrating the deformations of the sample tube during piercing of the stopper (FIG. 2) and during extraction of the needle (FIG. 3)

The needle 7 is thus subjected to a translation until it reaches the stopper 2. When the tip of the needle contacts the stopper 2, the resulting load moment at the level of the motor M modifies the characteristics of the supply current. These modifications are detected by the detector D which transmits corresponding information to the processor P. During perforation of the stopper 2, the needle 7 subjects the rubber body 3 to a stress generating a downward deformation (cambering) of said body and, at the same time, an increase in the volume of the cavity (FIG. 2). This deformation thus increases the pressure inside the tube 1. Even in the event of this excess pressure being offset by the circulation of gas in the needle 7, the pressure inside the tube 1 remains undetermined. As a result, the quantity sampled off will be imprecise.

Figure 3:
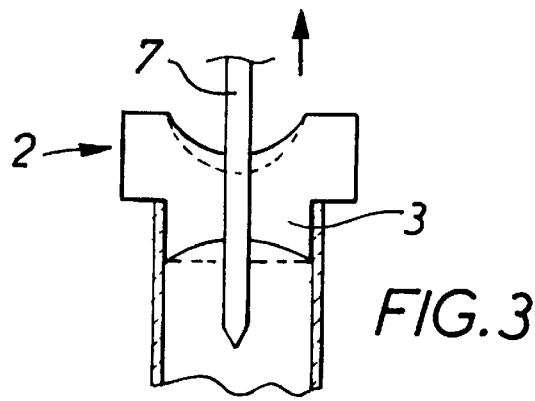
Figure 4:
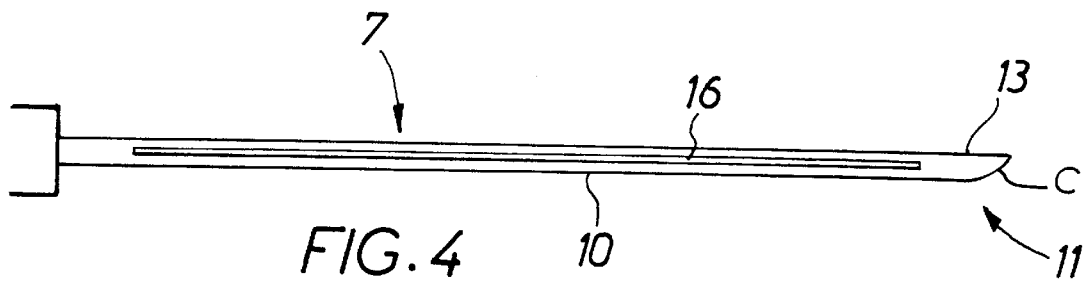
FIG. 4 is a side view of the needle used according to the invention, in a plane parallel to the longitudinal plane of symmetry of the needle.
Figure 5:
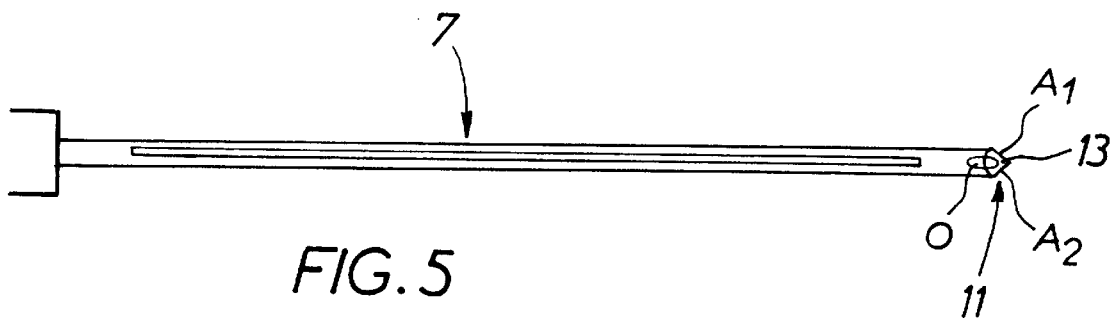
FIG. 5 is a side view of the needle at 90° from the view shown in FIG. 4.
Figure 7:
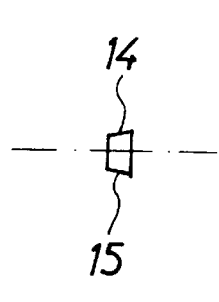
FIGS. 7 and 8 are sectional views respectively along A/A' and B/B' of FIG. 6.
Figure 6:
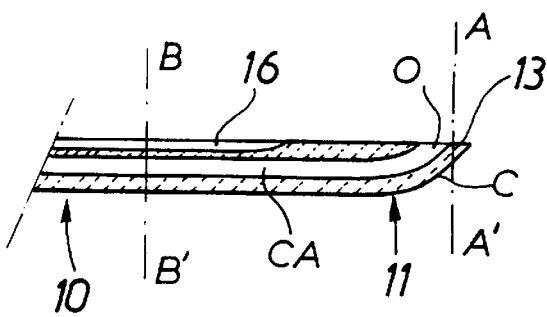
FIG. 6 is an axial section of the tip of the needle.
Figure 8:
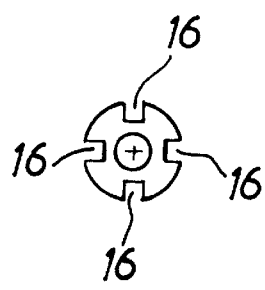
Figure 9:
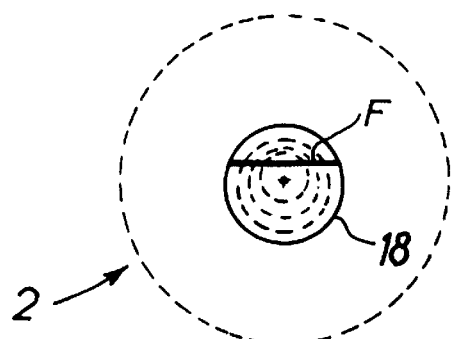
FIG. 9 is a schematic representation illustrating the principle of the piercing of the stopper by way of the needle represented in FIGS. 4 to 8.

During extraction of the needle 7, the body 3 of the stopper 2 is subjected to a stress that is the reverse of the previous stress: the underside of the stopper body 2 is deformed to take on a concave shape while generating a depression inside the tube (FIG. 3). This depression will cause the liquid sampled off by the needle to be subjected to a suction which adds a further degree of imprecision to the quantity sampled off. This dual phenomenon further varies as a function of the level of the sample inside the tube 1.

Of course, to these sources of imprecision must be added the cause arising from the fact that a conventional needle acts like a hollow punch and cuts out a portion of rubber susceptible of at least partially blocking the needle 7.

As illustrated in FIGS. 4 to 8, the needle embodying the invention enables these drawbacks to be avoided.

This needle 7 comprises a hollow cylindrical body 10 of which the pointed end 11 is obtained by a cranking of the end of the body 10 and then by machining of said cranked end so as to produce a face 13 at a tangent to a generating line of the body 10 and perpendicular to the plane of symmetry of said cranked part C.

We thus obtain a flat machined face 13 of which the ovoidal end constitutes the start of the cutting edge. This cutting edge $A_1$, $A_2$ is sharpened by grinding of the two lateral faces 14, 15 conferring it with a pointed V-shaped form visible in FIG. 5.

Furthermore, the outer surface of the body 7 comprises four longitudinal grooves 16 diametrically opposed two by two, each of square cross-section.

These longitudinal grooves 16, which are made over a large portion of the length of the needle 7, terminate at a predetermined distance from the tip 11 so as to never be in contact with the liquid to be sampled off.

By way of these arrangements, during perforation of the stopper 2, the cutting edges $A_1$, $A_2$ of the tip 11 perform a rectilinear cut in the rubber, thus avoiding any hollow punch phenomenon. This slit F is then elastically enlarged on one side by the cranked portion until it reaches the body 10 by gradually taking on a circular shape 18. During this perforation, the machined face 13 into which the outlet hole O of the needle channel CA opens, slides on the face of the slit upon which only the slightest of stresses is exerted and which is only very slightly deformed (it remains flat). As a result, the rubber does not penetrate the hole O and there is no risk of exterior plugging.

Once the tip of the needle 7 has passed through the stopper 2 and the grooves 16 emerge inside the tube 1, an aeration of the interior volume of the tube 1 is obtained. The pressure in the tube at the time of the sampling off phase is thus reduced to a constant value (atmospheric pressure). The quantities sampled off are therefore no longer subject to the above-mentioned pressure variations and are therefore relatively precise.

During extraction of the needle 7, the tip of the needle which has been in contact with the sample is wiped all the better that no rubber has been removed and that the slit closes up gradually as the cross-section of the needle decreases.

When the needle is extracted, the slit is completely sealed and the prestress exerted by the tube on the body ensures perfect tightness.

What is claimed is:

1. Device for the sampling and/or injecting of liquid into a receptacle sealed by a stopper, this device using a hollow needle that is axially mobile so as to be capable of perforating the stopper and which comprises a pointed tip having at least one cutting edge at a tangent to a generating line of the cylindrical body of the needle, an oblique shape connecting the edge to said cylindrical body and a lateral outlet hole of the channel centered on said generating line at a location distant from the edge this hole being angled perpendicularly to the longitudinal axis of the needle, wherein the said hole and said edge extend in a same plane at a tangent to said generating line.

2. Device as claimed in claim 1, wherein the said oblique shape consists of a cranking of the end of the cylindrical body.

3. Device as claimed in claim 2, wherein the said tangential plane is a machined plane perpendicular to the plane of symmetry of the cranking.

4. Device as claimed in claim 3, wherein the cylindrical body of the needle comprises, in its outer cylindrical surface, at least one axial groove ending at a predetermined distance from the tip of the needle.

5. Device as claimed in claim 4, wherein the said groove is of rectangular cross-section.

6. Device as claimed in claim 4, wherein the said body comprises four longitudinal grooves diametrically opposed two by two.

7. Device as claimed in claim 4, wherein the said groove is of square cross-section.

8. Device as claimed claim 1, wherein the cutting edge has a pointed shape thanks to the grinding of two lateral faces.

9. Device as claimed claim 1, wherein the motion of the needle is controlled by an electric motor supplied by a circuit including a detector capable of detecting a parameter representative of the load moment generated when the tip of the needle enters into contact with the stopper.

* * * * *